United States Patent [19]

Wydro et al.

[11] Patent Number: 5,258,288
[45] Date of Patent: Nov. 2, 1993

[54] VECTOR CONTAINING DNA ENCODING MATURE HUMAN PROTEIN S

[75] Inventors: Robert Wydro, Framingham; Edward Cohen, Natick; William Dackowski, Hopkinton, all of Mass.; Johan Stenflo, Malmo, Sweden; Ake Lundwall, Lund, Sweden; Bjorn Dahlback, Malmo, Sweden

[73] Assignee: Genzyme Corporation, Cambridge, Mass.

[21] Appl. No.: 890,401

[22] Filed: Jul. 25, 1986

[51] Int. Cl.$^5$ .............. C12P 21/02; C12P 19/34; C12N 15/00; C12N 7/00; C12N 5/00; C07K 3/00; C07H 15/12

[52] U.S. Cl. .............. 435/69.6; 435/69.1; 435/172.3; 435/320.1; 435/235.1; 435/240.2; 536/23.5; 530/350; 935/19; 935/32; 935/41; 935/57; 935/62; 935/70

[58] Field of Search .............. 435/68, 172.3, 320, 435/240, 69.1, 91, 235, 240.1, 320.1, 252.3; 530/350; 536/27

[56] References Cited

U.S. PATENT DOCUMENTS 4,419,446 12/1983 Howley et al. .............. 435/68

OTHER PUBLICATIONS

DiScipio, R. G. et al Biochemistry vol. 18 pp. 899–904 (1979).
Maniatis, T. et al Molecular Cloning, a Laboratory Manual, Cold Spring Harbor Laboratory (1982).
Jenne, D. et al EMBO J. vol. 4 pp. 3153–3157 (1985).
Dahlback, B. et al xth International Congress on Thrombosis and Haemastasis vol. 54, No. 1 Jul. 14, 1985 p. 56.
Pavlakis et al Proc Nat'l Acad Sci USA vol 80 pp. 397–401 (1983).
Suggs, S. V. et al Proc Nat'l Acad Sci USA vol. 78 pp. 6613–6617 (1981).
Davie, E. W. et al ICSU Short Rep 1 (Adv. Gene Technology) 1984 pp. 100–105.
Gubler et al Gene vol. 25 pp. 263–269 (1983).
Hoskins et al Proc Non Acad Sci, USA vol. 84 pp. 349–353 (1987).
Comp et al. (1984) J. Clin. Invest. 74:2082.
Schwarz et al. (1984) Blood 64:1297.
Walker (1984) Seminars in Thrombosis and Hemostasis 10:131.
Broekmans et al. (1985).
Dahlback (1984) Seminars in Thrombosis and Hemostasis 10:139.
Suzuki (1984) J. Biochem. 96:455.
de Fouw et al. (1986) Blood 67:1186.

Primary Examiner—Joan Ellis
Attorney, Agent, or Firm—Fish & Richardson

[57] ABSTRACT

Disclosed are a transformed mammalian cell that produces biologically active Protein S, and a vector for effecting the transformation of the cell. produces biologically active human Protein S, and the vector used to effect the transgenesis of the cell. The vector disclosed includes DNA encoding mature human Protein S, under the transcriptional control of a eukaryotic metallothionein gene, and also includes the transforming region of the bovine papilloma virus genome, and a fragment of SV40 DNA.

11 Claims, 13 Drawing Sheets

FIG. 2-1

```
                                         Met Arg Val Leu Gly Gly Arg Thr Gly Thr
CCGCCGCTTCTGCCCAAGCCTCCGCCCGTTTCGCC ATG AGG GTC CTA GGT GGG CGC ACC GGG ACG
Leu Ser Arg Gln His Ala Ser Gln Val Leu Ile Arg Arg Arg Arg Ala Asn Thr Leu
TTG TCG AGG CAA CAT GCT TCA CAA GTC CTG ATT AGG AGA CGC CGT GCA AAT ACA TTG
Leu Cys Asn Lys Glu Glu Ala Arg Glu Ile Phe Glu Asn Asn Pro Glu Thr Glu Tyr
CTG TGC AAT AAA GAA GAA GCC AGG GAA ATC TTT GAA AAT AAC CCG GAA ACG GAA TAT
Phe Thr Ala Ala Arg Leu Ser Thr Asn Ala Tyr Pro Asp Leu Arg Ser Cys Val Asn
TTC ACT GCT GCT CGT CTG TCA ACT AAT GCT TAC CCT GAC CTG AGG AGC TGT GTC AAT
Met Thr Cys Lys Asp Gly Gln Ala Thr Phe Thr Cys Ile Cys Lys Ser Gly Trp Gln
ATG ACC TGC AAA GAT GGC CAA GCG ACA TTC ACT TGC ATT TGT AAA TCA GGT TGG CAA
Ile Asn Gly Gly Cys Ser Gln Ile Cys Glu Asn Thr Pro Gly Ser Tyr His Cys Ser
ATA AAT GGA GGT TGC AGC CAG ATT TGT GAA AAC ACA CCT GGA AGT TAC CAC TGT TCC
Val Asp Glu Cys Val Leu Lys Pro Ser Ile Cys Gly Thr Ala Val Cys Lys Asn Ile
GTG GAT GAA TGC GTT TTA AAG CCA AGC ATT TGT GGC ACA GCT GTG TGC AAG AAC ATC
Val Ser Lys Ser Cys Asp Asp Val Asp Glu Cys Ala Glu Asn Leu Cys Ala Gln Leu
GTA TCA AAG TCT TGT GAC GAT GTG GAT GAA TGC GCT GAG AAC TTG TGT GCT CAA CTT
Gly Phe Lys Leu Ala Gln Asp Gln Lys Ser Cys Glu Ala Val Pro Val Cys Leu Pro
GGA TTC AAA CTT GCC CAA GAT CAG AAG AGT TGT GAG GCT GTT CCA GTG TGC CTT CCT
Val Gly Val Val Leu Tyr Leu Lys Phe Arg Leu Pro Glu Thr Thr Arg Phe Ser Ala
GTA GGG GTT GTT TTG TAT TTA AAA TTT CGT TTG CCA GAA ACT ACC AGA TTT TCA GCT
Glu Ser Ser Asp His Ser Ala Trp Phe Leu Ile Ala Leu Arg Glu Gly Lys Ile Glu
GAA TCT TCT GAT CAC TCA GCT TGG TTC CTG ATT GCG CTT CGT GAG GGA AAG ATT GAA
Val Ile Asn Asp Gly Leu Trp His Met Val Ser Val Glu Glu Leu Glu Gln Ser Ile
GTT ATT AAT GAT GGT TTA TGG CAT ATG GTC TCT GTG GAA GAA TTA GAA CAG AGT ATT
Ser Leu Phe Lys Pro Thr Asn Gly Phe Leu Glu Thr Lys Val Tyr Phe Ala Gly Val
AGC CTT TTT AAG CCC ACC AAT GGG TTT CTA GAA ACC AAA GTA TAC TTT GCA GGA GTA
Asp Gly Cys Ile Arg Gly Trp Asn Leu Met Asn Gln Gly Thr Ser Gly Val Lys Glu
GAT GGA TGT ATT CGA GGC TGG AAT TTG ATG AAT CAA GGA ACT TCA GGA GTA AAG GAA
Gly Ser Tyr Tyr Pro Gly Thr Gly Val Ala Gln Phe Ser Ile Asn Tyr Lys Asn Glu
GGT TCC TAC TAT CCT GGT ACT GGA GTT GCT CAG TTT AGC ATA AAT TAT AAG AAT GAA
Ser Ala Gly Thr Gly Val Met Leu Ala Leu Val Ser Asp Asn Thr Val Pro Phe Ala
TCA GCG GGC ACC GGT GTT ATG TTG GCC TTG GTT TCC GAT AAC ACA GTG CCC TTT GCC
Ser Val Glu Ser Met Val Ile Gly Arg Ile Glu Ala Ile Ser Leu Cys Ser Asp Gln
TCT GTT GAA AGT ATG GTA ATA GGT CGG ATA GAG GCC ATA AGT CTG TGT TCC GAT CAG
Thr Gln Leu Arg Lys Asp Ser Phe His Ser Glu Asp Phe Gln Arg Gln Phe Ala Ile
ACT CAA CTT AGA AAG GAT AGC TTC CAC TCT GAA GAC TTT CAA AGA CAA TTT GCC ATC
Pro Asp Val Pro Phe Ser Ala Thr Pro Val Asn Ala Phe Tyr Gln Gly Cys Met Glu
CCA GAT GTT CCA TTC AGT GCC ACA CCA GTG AAT GCC TTT TAT CAA GGC TGT ATG GAA
His Asn Asp Ile Arg Ala His Ser Cys Pro Ser Val Trp Gln Lys Thr Lys His Thr
CAT AAT GAT ATT AGA GCT CAC TCG TGT CCA TCA GTT TGG CAG AAG ACA AAG CAT ACT
TAATAGCTGAAGAATTTTACCTACAATGTGCATATCTTGATTATTTTGTGGTACTTTAACTTTCCTGAAATTTTAA
ACCTCTGTTGCTCTCTAGAAATTAATGAAACCTATAAAATTTTTAATTTGAAATTTTTGTGACAAATGACATTTC
```

```
            Leu Leu Ala Cys Leu Ala Leu Val Leu Pro Val Leu Glu Ala Asn Phe
            CTG CTG GCA TGC CTC GCC CTA GTG CTT CCC GTC TTG GAG GCT AAC TTT     113

Leu Glu Glu Thr Lys Lys Gly Asn Leu Glu Arg Glu Cys Ile Glu Glu     20
            CTT GAA GAA ACG AAA AAG GGC AAT CTT GAA AGA GAA TGC ATT GAA GAA     218

Phe Tyr Pro Lys Tyr Leu Gly Cys Leu Gly Ser Phe Arg Ala Gly Leu     55
            TTT TAT CCA AAA TAT TTA GGT TGT CTT GGC TCT TTC AGA GCT GGA TTA     323       FIG.

Ala Ile Ser Asp Gln Cys Asn Pro Leu Pro Cys Asn Glu Asp Gly Phe     90        2-2
            GCC ATT TCG GAC CAG TGT AAT CCT CTG CCA TGC AAT GAA GAT GGA TTT     428

Gly Glu Lys Cys Glu Ser Asp Ile Asn Glu Cys Lys Asp Pro Val Asn     125
            GGA GAA AAG TGT GAA TCT GAT ATA AAT GAA TGC AAA GAT CCT GTA AAT     533

Cys Lys Asn Gly Phe Val Met Leu Ser Asn Lys Lys Asp Cys Lys Asp     160
            TGT AAA AAT GGT TTT GTT ATG CTT TCA AAT AAA AAG GAC TGC AAA GAT     638

Pro Gly Asp Phe Glu Cys Glu Cys Ala Glu Gly Tyr Lys Tyr Asn Pro     195
            CCA GGA GAC TTT GAA TGT GAA TGT GCT GAA GGC TAC AAA TAC AAT CCC     743

Cys Val Asn Tyr Pro Gly Gly Tyr Ser Cys Tyr Cys Asp Gly Lys Lys     230
            TGT GTC AAT TAC CCT GGA GGT TAC TCT TGT TAC TGT GAC GGA AAG AAA     848

Leu Asp Leu Asp Lys Asn Tyr Gly Leu Leu Tyr Leu Ala Glu Gln Phe     265
            TTG GAC CTT GAC AAA AAT TAT GAA TTG CTT TAC TTG GCA GAG CAG TTT     953

Glu Phe Asp Phe Arg Thr Tyr Asp Ser Glu Gly Val Ile Leu Tyr Ala     300
            GAA TTT GAT TTC CGG ACA TAT GAT TCA GAA GGT GTT ATC CTG TAT GCA     1056

Ile Gln Phe Lys Asn Glu Lys Thr Thr Lys Met Thr Thr Gly Gly Lys     335
            ATT CAG TTC AAG AAT GAA AAG ACA ACC AAA ATG ACA ACT GGA GGC AAA     1163

Ser Val Lys Ile Ala Lys Glu Ala Val Met Asn Ile Asn Lys Pro Gly     370
            AGT GTA AAA ATA GCT AAA GAA GCT GTA ATG AAT ATA AAT AAG CCT GGA     1266

Pro Arg Lys Met Glu Asn Ala Leu Ile Arg Pro Ile Asn Pro Arg Leu     405
            CCT CGG AAA ATG GAA AAT GCA CTC ATT AGA CCG ATT AAC CCT CGT CTA     1373

Ile Ile Gln Glu Lys Gln Asn Lys His Cys Leu Val Asn Val Glu Lys     440
            ATC ATT CAA GAA AAA CAA AAT AAG CAT TGT CTT GTC AAT GTG GAG AAG     1478

Ser Asn Pro Glu Ala Trp Gln Ile Asn Val Ser Leu Asn Ile Arg Pro     475
            TCC AAT CCT GAG GCT TGG CAA ATC AAT GTG TCC TTG AAT ATT CGC CCA     1583

Leu Ser Leu Val Asp Ser Ala Thr Glu Lys Leu Gln Asp Ile Leu Val     510
            TTG TCC TTG GTG GAT TCC GCC ACT GAA AAG CTT CAG GAT ATC CTG GTA     1688

Gln Thr Phe Leu Glu Ile Arg Val Asn Arg Asn Asn Leu Glu Leu Ser     545
            CAA ACC TTT CTG GAA ATC AGA GTC AAC AGA AAC AAT TTG GAA CTA TCG     1793

Leu Asp Glu Ala Met Lys Gly Thr Val Val Thr Tyr Leu Gly Gly Leu     580
            TTG GAT GAA GCA ATG AAA GGA ACA GTG GTC ACT TAC CTG GGT GGC CTT     1898

Val Asn Ile Asn Gly Val Gln Val Asp Leu Asp Glu Ala Ile Ser Lys     615
            GTG AAC ATT AAT GGT GTA CAG GTG GAT TTG GAT GAA GCC ATT TCT AAA     2003

TAAGGCATTTTTTCTCTGCTGATAATACCTTTTTTCCTGTGTGTAATTATACTTATGTTTCAA                         2122

AAAGGTCCTTTTTCAAGAAAACAAGATTCTCTTGTGATATGAATCATATTAAAAATGTTCTT                          2260

TTCTTTTTTATGTTTGTAAAAGTAAAGTTTAATTTTATCATCATGaaaaaaaaaaaaaaa
```

```
GAA TTC CGA AGA CCC AAA AGC AGA AAC CCC TGA TAA AAC CAT CAG ACT TCA
AAT TTT CTC CCA CCA GTT GCC TCC CAC AAC ATG TGG CAA TTA TGG GAG TTC
                                            Leu Ser Lys Gln Gln
GAA AAG AGT CTC ATA AGA TGC AAG TGA GGA AGA GTT TTG TCA AAG CAA CAG
Lys Gln Gly Asn Leu Glu Arg Glu Cys Ile Glu Glu Leu Cys Asn Lys Glu
AAA CAG GGT AAT CTT GAA AGA GAA TGC ATC GAA GAA CTG TGC AAT AAA GAA
Tyr Leu Val Cys Leu Arg Ser Phe Gln Thr Gly Leu Phe Thr Ala Ala Arg
TAC TTA GTT TGT CTT CGC TCT TTT CAA ACT GGG TTA TTC ACT GCT GCA CGT
Gln Cys Ser Pro Leu Pro Cys Asn Glu Asp Gly Tyr Met Ser Cys Lys Asp
CAG TGT AGT CCT CTG CCA TGC AAT GAA GAT GGA TAT ATG AGC TGC AAA GAT
Glu Phe Asp Ile Asn Glu Cys Lys Asp Pro Ser Asn Ile Asn Gly Gly Cys
GAA TTT GAC ATA AAT GAA TGC AAA GAT CCC TCA AAT ATA AAT GGA GGT TGC
Phe Val Met Leu Ser Asn Lys Lys Asp Cys Lys Asp Val Asp Glu Cys Ser
TTT GTT ATG CTT TCA AAT AAG AAA GAT TGT AAA GAT GTG GAT GAA TGC TCT
Glu Cys Glu Cys Pro Glu Gly Tyr Arg Tyr Asn Leu Lys Ser Lys Ser Cys
GAA TGT GAA TGC CCC GAA GGC TAC AGA TAT AAT CTC AAA TCA AAG TCT TGT
Pro Gly Gly His Thr Cys Tyr Cys Asp Gly Lys Lys Gly Phe Lys Leu Ala
CCT GGA GGT CAC ACT TGC TAT TGT GAT GGG AAG AAA GGA TTC AAA CTT GCC
Thr Lys Tyr Glu Leu Leu Tyr Leu Ala Glu Gln Phe Ala Gly Val Val Leu
ACA AAG TAT GAA TTA CTT TAC TTG GCG GAG CAG TTT GCA GGG GTT GTT TTA
Arg Thr Tyr Asp Ser Glu Gly Val Ile Leu Tyr Ala Glu Ser Ile Tyr His
CGG ACA TAT GAT TCA GAA GGC GTG ATA CTG TAC GCA GAA TCT ATC TAT CAC
Asn Glu His Thr Ser Lys Ile Thr Thr Gly Gly Asp Val Ile Asn Asn Gly
AAT GAA CAT ACA TCC AAA ATC ACA ACT GGA GGT GAT GTT ATT AAT AAT GGT
Ala Lys Glu Ala Val Met Asp Ile Asn Lys Pro Gly Pro Leu Phe Lys Pro
GCT AAA GAA GCT GTG ATG GAT ATA AAT AAA CCT GGA CCC CTT TTT AAG CCG
Glu Ser Glu Leu Ile Lys Pro Ile Asn Pro Arg Leu Asp Gly Cys Ile Arg
GAA AGT GAA CTC ATT AAA CCG ATT AAC CCT CGT CTA GAT GGA TGT ATA CGA
Lys Gln Asn Lys His Cys Leu Val Thr Val Glu Lys Gly Ser Tyr Tyr Pro
AAA CAA AAT AAG CAT TGC CTG GTT ACT GTG GAG AAG GGC TCC TAC TAT CCT
Gly Trp His Val Asn Val Thr Leu Asn Ile Arg Pro Ser Thr Gly Thr Gly
GGT TGG CAT GTA AAT GTG ACC TTG AAT ATT CGT CCA TCC ACG GGC ACT GGT
Val Asp Ser Thr Ser Glu Lys Ser Gln Asp Ile Leu Leu Ser Val Glu Asn
GTG GAC TCC ACC TCT GAA AAA TCA CAG GAT ATT CTG TTA TCT GTT GAA AAT
Leu Glu Phe Arg Val Asn Arg Asn Asn Leu Glu Leu Ser Thr Pro Leu Lys
CTG GAA TTT AGA GTC AAC AGA AAC AAT CTG GAG TTG TCG ACA CCA CTT AAA
Ala Met Lys Ala Lys Val Ala Thr Tyr Leu Gly Gly Leu Pro Asp Val Pro
GCA ATG AAA GCA AAA GTG GCC ACA TAC CTG GGT GGC CTT CCA GAT GTT CCA
Asn Gly Val Gln Leu Asp Leu Asp Glu Ala Ile Ser Lys His Asn Asp Ile
AAT GGT GTA CAG TTG GAT CTG GAT GAA GCC ATT TCT AAA CAT AAT GAT ATT
```

FIG. 4A-1

```
                                                                                    TGA GAC TTA TTC ACC ACC ATG AGA ACA GTA TGG GGG AAA CCA CCC CAG TGA TTC   105
                                                                                    AAT TAA AGA TGA GAT TTG GAT GGG GAC ACA GAG CCA AAC CAT ATC AAG TAC AAA   210
Ala Ser Gln Val Leu Val Arg Lys Arg Arg Ala Asp Ser Leu Leu Glu Glu Thr     8
GCT TCA CAA GTC CTG GTT AGG AAG CGT CGT GCA AAT TCT TTA CTT GAA GAA ACC   315
Glu Ala Arg Glu Val Phe Glu Asn Asp Pro Glu Thr Asp Tyr Phe Tyr Pro Lys   43
GAA GCC AGG GAG GTC TTT GAA AAT GAC CCG GAA ACG GAT TAT TTT TAT CCA AAA   420
Gln Ser Thr Asn Ala Tyr Pro Asp Leu Arg Ser Cys Val Asn Ala Ile Pro Asp   78
CAG TCA ACT AAT GCT TAT CCT GAC CTA AGA AGC TGT GTC AAT GCC ATT CCA GAC   525
Gly Lys Ala Ser Phe Thr Cys Thr Cys Lys Pro Gly Trp Gln Gly Glu Lys Cys  113
GGA AAA GCT TCT TTT ACT TGC ACT TGT AAA CCA GGT TGG CAA GGA GAA AAG TGT   630
Ser Gln Ile Cys Asp Asn Thr Pro Gly Ser Tyr His Cys Ser Cys Lys Asn Gly  148
AGT CAA ATT TGT GAT AAT ACA CCT GGA AGT TAC CAC TGT TCC TGT AAA AAT GGT   735
Leu Lys Pro Ser Ile Cys Gly Thr Ala Val Cys Lys Asn Ile Leu Gly Asp Phe  183
TTG AAG CCA AGC ATT TGT GGC ACA GCT GTG TGC AAG AAC ATC CTA GGA GAT TTT   840
Glu Asp Ile Asp Glu Cys Ser Glu Asn Met Cys Ala Gln Leu Cys Val Asn Tyr  218
GAA GAT ATA GAT GAA TGC TCT GAG AAC ATG TGT GCT CAG CTT TGT GTC AAT TAC   945
Gln Asp Gln Lys Ser Cys Glu Val Val Ser Val Cys Leu Pro Leu Asn Leu Asp  253
CAA GAT CAG AAG AGT TGT GAG GTT GTT TCA GTG TGC CTT CCC TTG AAC CTT GAC  1050
Tyr Leu Lys Phe Arg Leu Pro Glu Ile Ser Arg Phe Ser Ala Glu Phe Asp Phe  288
TAT TTA AAA TTT CGT TTG CCA GAA ATC AGC AGA TTT TCA GCA GAA TTT GAT TTC  1155
Ser Ala Trp Leu Leu Ile Ala Leu Arg Gly Gly Lys Ile Glu Val Gln Leu Lys  323
TCA GCG TGG CTC CTG ATT GCA CTT CGT GGT GGA AAG ATT GAA GTT CAG CTT AAG  1260
Leu Trp Asn Met Val Ser Val Glu Glu Leu Glu His Ser Ile Ser Ile Lys Ile  358
CTA TGG AAT ATG GTG TCT GTG GAA GAA TTA GAA CAT AGT ATT AGC ATT AAA ATA  1365
Glu Asn Gly Leu Leu Glu Thr Lys Val Tyr Phe Ala Gly Phe Pro Arg Lys Val  393
GAA AAT GGA TTG CTG GAA ACC AAA GTA TAC TTT GCA GGA TTC CCT CGG AAA GTG  1470
Ser Trp Asn Leu Met Lys Gln Gly Ala Ser Gly Ile Lys Glu Ile Ile Gln Glu  428
AGC TGG AAT TTG ATG AAG CAA GGA GCT TCT GGA ATA AAG GAA ATT ATT CAA GAA  1575
Gly Ser Gly Ile Ala Gln Phe His Ile Asp Tyr Asn Asn Val Ser Ser Ala Glu  463
GGT TCT GGA ATT GCT CAA TTT CAC ATA GAT TAT AAT AAT GTA TCC AGT GCT GAG  1680
Val Met Leu Ala Leu Val Ser Gly Asn Asn Thr Val Pro Phe Ala Val Ser Leu  498
GTT ATG CTT GCC TTG GTT TCT GGT AAC AAC ACA GTG CCC TTT GCT GTG TCC TTG  1785
Thr Val Ile Tyr Arg Ile Gln Ala Leu Ser Leu Cys Ser Asp Gln Gln Ser His  533
ACT GTA ATA TAT CGG ATA CAG GCC CTA AGT CTA TGT TCC GAT CAA CAA TCT CAT  1890
Ile Glu Thr Ile Ser His Glu Asp Leu Gln Arg Gln Leu Ala Val Leu Asp Lys  568
ATA GAA ACC ATC TCC CAT GAA GAC CTT CAA AGA CAA CTT GCC GTC TTG GAC AAA  1995
Phe Ser Ala Thr Pro Val Asn Ala Phe Tyr Asn Gly Cys Met Glu Val Asn Ile  603
TTC AGT GCC ACA CCA GTG AAT GCC TTT TAT AAT GGC TGC ATG GAA GTG AAT ATT  2100
Arg Ala His Ser Cys Pro Ser Val Trp Lys Lys Thr Lys Asn Ser
AGA GCT CAC TCA TGT CCA TCA GTT TGG AAA AAG ACA AAG AAT TCT TAA GGC ATC  2205
```

FIG. 4A-2

```
TTT TCT CTG CTT ATA ATA CCT TTT CCT TGT GTG TAA TTA TAC TTA TGT TTC
CCT TTC CTG GGA TTT TTA AAA GGT CCT TTG TCA AGG AAA AAA TTC TGT TGT
AAA TAA CAA TTT TAA ATT TGA ATT TTT TTC CTA CAA ATG ACA GTT TCA ATT
CCT ATG TTT TTT TCA GAA ACC AAG GAA GTA ACC TCA AAC AAA AGT GCG TGT
TCC TGA TGA AGG CAG AGA TGG TGG TCT ATT AAA TAT GA TTG AAT GGA
ATC TTT CTC TTG TGT GCC TTC ACA TTT AAA CCA GTA TCT TTA TTG AAT TAG
CCT GCA GTC TGT CAG GAT GAG ATA TCA GAT TAG GTT GGA TAG CTG GGG AAA
TTA CAA AAG ACA GAA TTC AGG GAT GGA AAG GAC AAT GAA CAA ATG TGG GAG
TGA TTG AAG TAC AAA AGG AAC TAT GAA AAC CAG AAC AAA TTT TAA CAA
AAG GAG GTA AGA TTG CCA GTA CGT GCC TGC TGC TAC TGT GAT GCA TTT CAA GTG
TCA CTG ACA GTT TTT AAC AAT AAA TTC TTT TCA CTG TAT TTT ATA TCA CTT
```

FIG. 4B-1

```
AAT AAC AGC TGA AGG GTT TTA TTT ACA ATG TCC AGT CTT TGA TTA TTT TGT GGT    2310
GAT ATA AAT CTC AGT AAA GAA ATT CTT ACT TCT CTT GCT ATT AAG AAT AGT GAA    2415
TTT GTT TGT AAA ACT AAA TTT TTA ATT TCA TCA TGA ACT AGT GTC TAA ATA        2520
AAT TAA ATA CTA TTA ATC ATA GCC AGA TAC TAT TTT GTT ATG TTT TTG TTT TTT   2625
GGG TCC TAA TGC CTT ATT TCA AAA CAA TTC CTC AGG GGC ACC AGC TTT GCC TTC   2730
AAA ACA AGT GGG ACA TAT TTT CCT GAG AGC ACA GTA ATC TTC TTC TTG GCA       2835
TCT GAA GTG GGT ACA TTT TTT AAA TTT TCC TGT GTG GGT CAC ACA AGG TCT ACA   2940
TTC ATA GTT TTC CTT GAA TCC AAC TTT TAA TTA CCA GTC TAA GTT GCC AAA ATG   3045
AAG GAC AAC CAC AGA GGG ATA TAC TGA ATA TCG TAT CAT TCT AAT CAA AGA AGT   3150
GCA GTT TTA TCA CGT TTG AAT CTA CCA TTC ATA GCC ATA GTT GTA TCA GAT GTT   3255
ATA ATA AAT CCG TGT ATA ATT TTA AAA AGG AAT TC
```

FIG. 4B-2

VECTOR CONTAINING DNA ENCODING MATURE HUMAN PROTEIN S

BACKGROUND OF THE INVENTION

This invention relates to Protein S and the use of recombinant DNA techniques to produce Protein S.

The coagulation cascade is a series of reactions, involving a number of plasma proteins, which occur in response to an injury. One of these plasma proteins, Protein S, helps ensure that blood does not clot in places other than the specific site of the injury. Protein S is a cofactor for the activated Protein C-induced cleavage of activated Factors V and VIII in the blood clotting pathway.

Recently Comp et al., (1984, J. Clin. Invest. 74: 2082) have suggested that Protein S deficiency may result in recurrent thrombotic disease; and Schwarz et al. (1984, Blood 64: 1297) have suggested that recurrent thrombotic disease may be the result of an inherited deficiency of Protein S.

SUMMARY OF THE INVENTION

In general, the invention features a vector containing DNA encoding mature human Protein S. As will be apparent from the detailed description below, "mature human Protein S" refers to the biologically active Protein S molecule without the leader sequence; thus the term as used herein is broad enough to include a DNA sequence (genomic or, more preferably, cDNA) which encodes at least the mature human Protein S, and which can also encode human or other (e.g., bovine) leader sequences, or hybrid leader sequences.

The vectors of the invention are used to transfect mammalian cells, e.g., rodent (e.g., mouse) cells to produce biologically active human Protein S, which can be used both therapeutically and diagnostically. Protein S can be used to treat congenital Protein S deficiency, and can also be administered in conjunction with Protein C, of which Protein S is a cofactor, to enhance its antithrombolytic activity. Protein S and Protein C can also be administered together in conjunction with the thrombolytic enzyme tissue plasminogen activator (t-PA) to enhance its activity and advantageously reduce the amount of t-PA required.

Other features and advantages of the invention will be apparent from the following description of the preferred embodiments thereof, and from the claims.

DESCRIPTION OF THE PREFERRED EMBODIMENTS

The drawings will first briefly be described.
Drawings

FIG. 2-1 to 2-2 are the nucleotide sequence of cDNA coding for bovine protein S, and the amino acid sequence of protein S; Gla stands for γ-carboxyglutamic acid; the Asp in position 93 is hydroxylated to β-hydroxyaspartic acid; the Asp in position 458 is glycosylated (arrowhead); the arrow denotes the start of the mature plasma protein; the polyadenylation signal is underlined;

Figure 5:
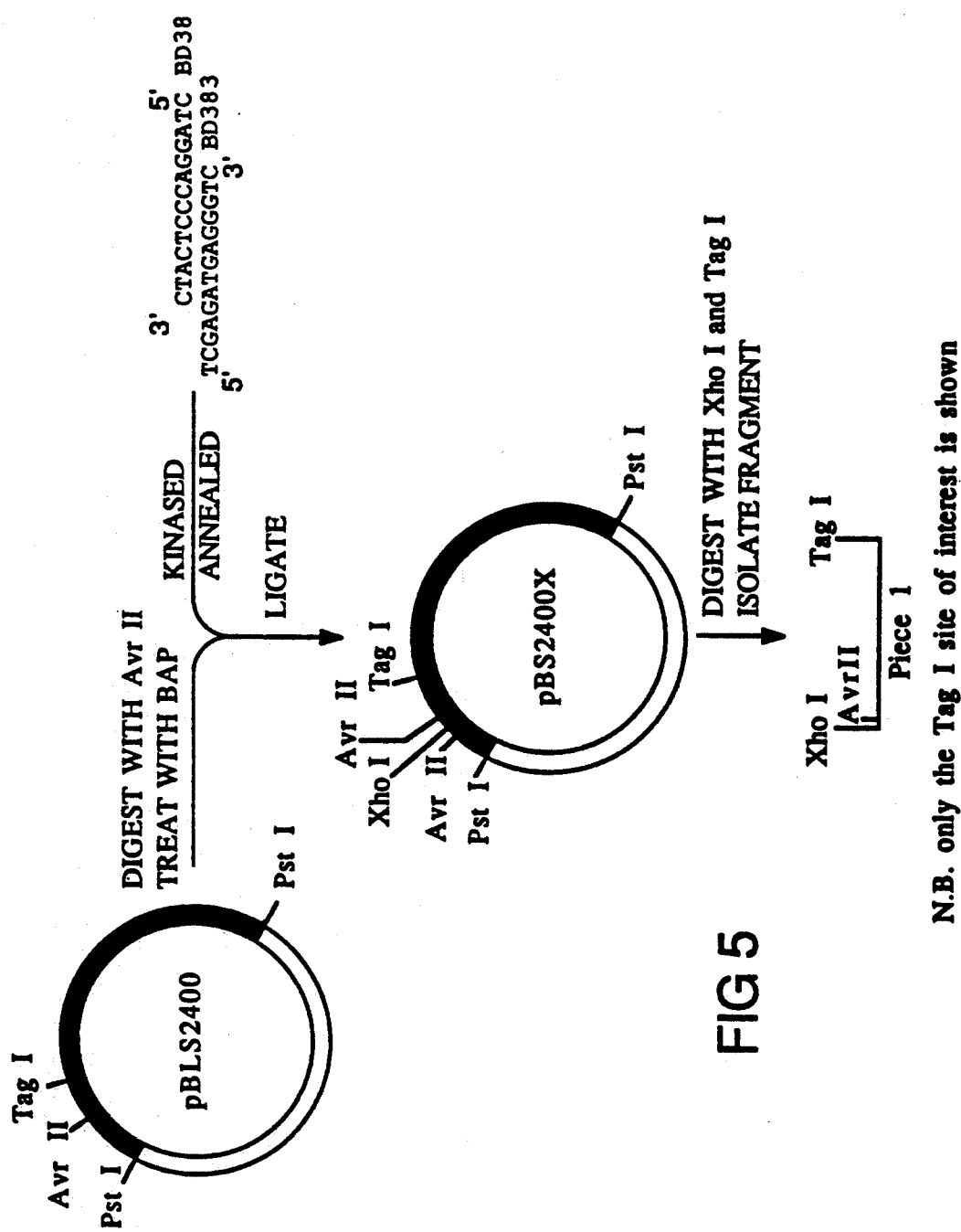
Figure 6:
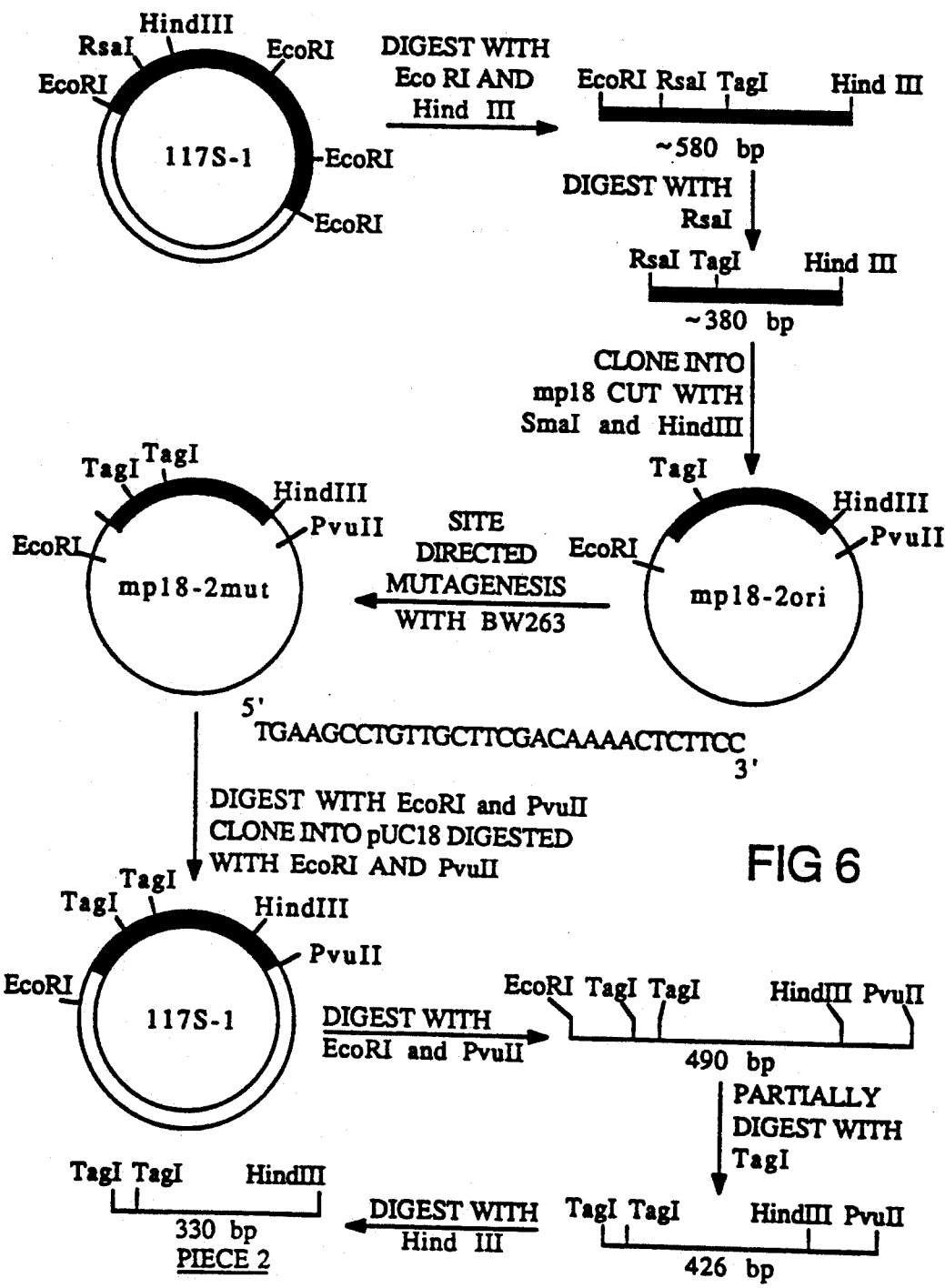
Figure 7:
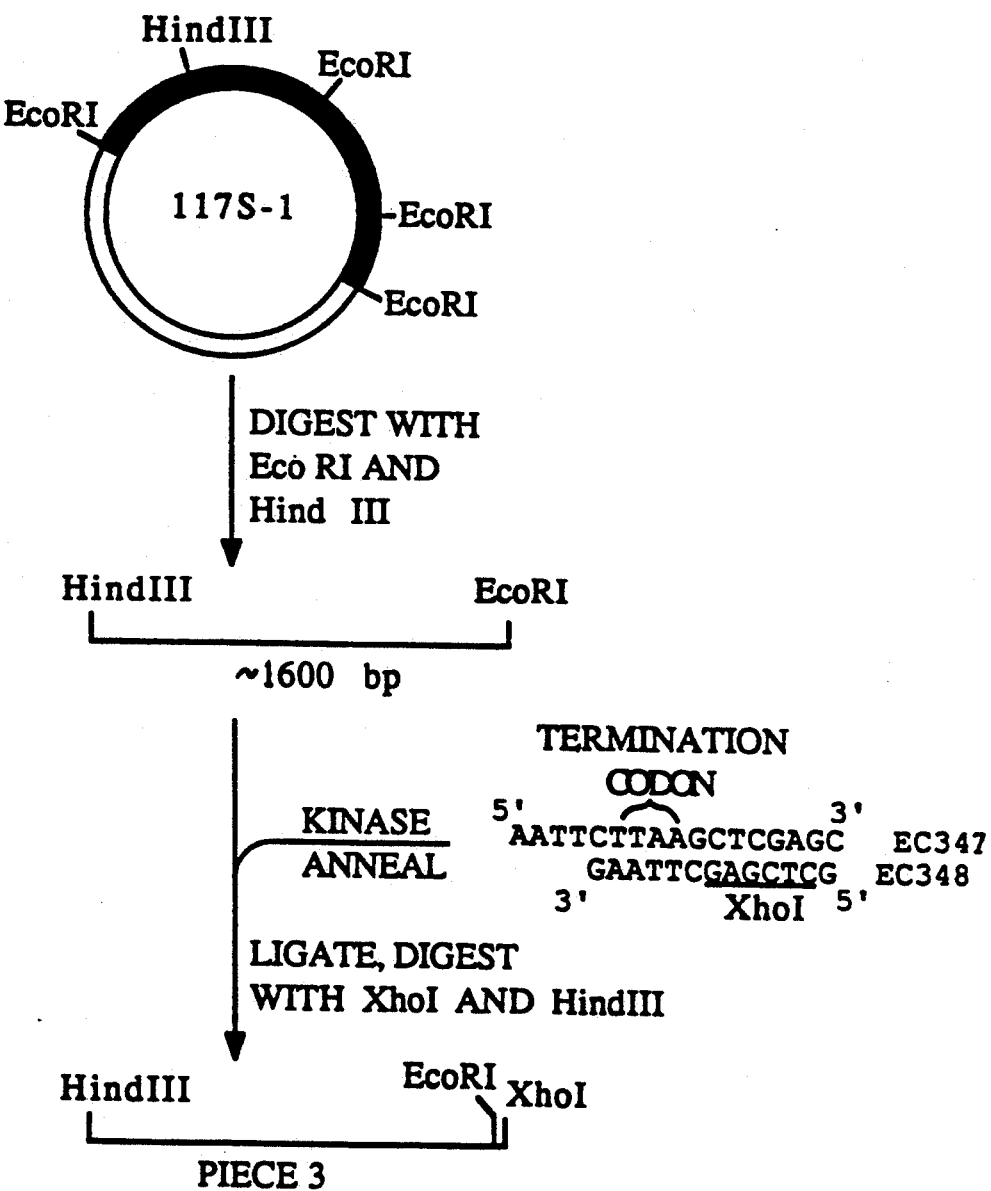
Figure 8:
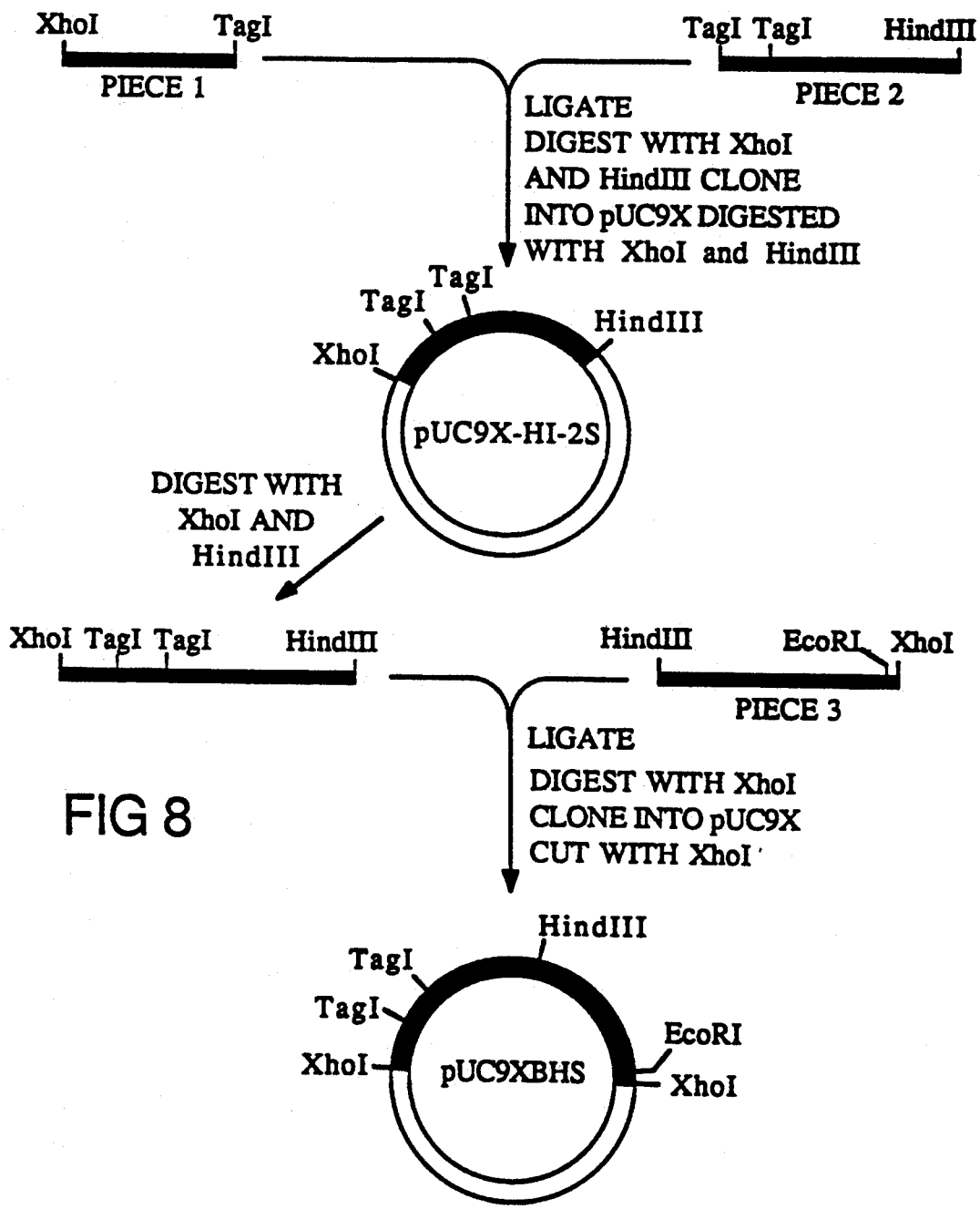

FIGS. 4A-1 to 4B-2 are the nucleotide sequence of cDNA coding for human Protein S, and its predicted amino acid sequence; the arrow denotes the start of the mature plasma protein; the eleven $NH_2$-terminal glutamic acid residues are assumed to be carboxylated (Gla); there are three potential glycosylation sites; i.e., Asn residues 458, 468 and 489; two putative polyadenylation signals are underlined;

FIGS. 5, 6, and 7 are diagrammatic representations of the preparation of pieces 1, 2, and 3 respectively, used for construction of pUC9XBHS;

FIG. 8 is a diagrammatic representation of the construction of pUC9XBHS; and

Figure 9:
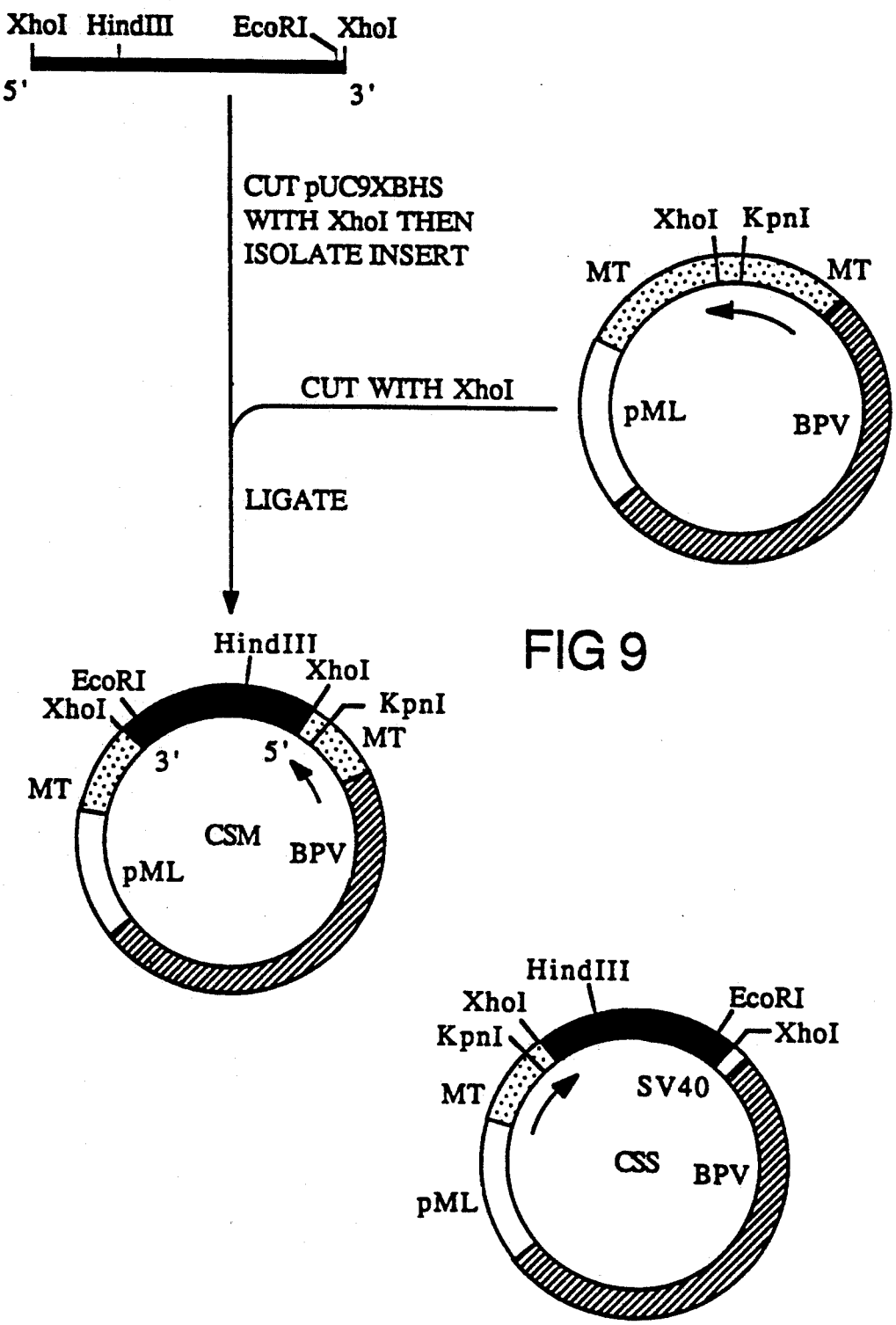

FIG. 9 is a diagrammatic representation of the construction of expression vectors, CSM and CSS, containing the human Protein S encoding DNA.

General Approach

In the example described below, the amino acid sequence of bovine protein S was determined and a cDNA sequence encoding the complete bovine Protein S isolated from a clone which hybridized to oligonucleotides prepared to a portion of mature bovine Protein S. A fragment derived from this clone was then used as a probe to identify a clone containing a cDNA sequence encoding the complete mature human Protein S. In order to facilitate its expression in mammalian cells, the DNA encoding the leader sequence of the bovine Protein S cDNA was spliced onto the human Protein S cDNA. These steps are now described in detail.

BOVINE PROTEIN S AMINO ACID SEQUENCE DETERMINATION

Protein S fragments were generated by enzymatic and chemical cleavages and the fragments purified by gel filtration and reverse phase high performance liquid chromatography (HPLC) as described by Dahlbach et al. (1986, J. Biol. Chem., in Press). Amino acid sequence was determined on a Beckman 890 C spinning cup sequencer, or on an Applied Biosystem gas phase sequencer; and the amino acid composition of peptides on a Beckman 6300 amino acid analyzer.

These data allowed identification and placement of 600 amino acids, contained in nine fragments, out of a total of 634. The order of the fragments in the sequence was tentatively determined. Approximately 130 fragments were analyzed either in the spinning cup or the gas phase sequencer. Most of Protein S was sequenced at least twice.

Two mixed oligonucleotide probes were synthesized; probe 1 was a 23-mer coding for amino acid residues 85-93 and probe 2 a 20-mer coding for residues 595-600:

```
5'-GTCATAAAACCATCCTCATTACA-3':   Probe 1
      G  C    G  T  G  G
         T
         G 5'ACTTCCATACAACCTTGATA-3':       Probe 2
   C      G  C    C  G
                  T
                  G
``` cDNA FOR BOVINE PROTEIN S

A bovine liver cDNA library (in pBR322) was screened by standard techniques (Grunstein and Hogness 1975, Proc. Nat.'l. Acad. Sci. 72:3961). A total of $10^5$ recombinants were screened with the two oligonucleotide probes. One clone, pBLS-200, was identified using probe 1. Sequence analysis showed it to have an insert that coded for amino acid residues 44–104. With probe 2, six clones were identified, but two had inserts less than 150 nucleotides long and were not examined further. The other four clones contained identical inserts coding for the 105 carboxyterminal amino acids and 76 nucleotides of the 3'nontranslated region. One of the four identical clones, pBLS-400, was used together with pBLS-200 to rescreen the library. Fifteen clones hybridized to pBLS-400, one to pBLS-200, and one to both. The latter, clone pBLS-2400 (shown in FIG. 1) carried a cDNA insert of approximately 2.4 kb suggesting that it contains the entire protein S coding sequence. In order to determine the nucleotide sequence, 60 μg of this plasmid DNA was digested with Pst 1. The cDNA insert was isolated, self-ligated, sonicated, and endrepaired. Subfragments of 300–600 base pairs were isolated and ligated into the SmaI site of the replicative form of the phage M 13 mp8, which was subsequently used to transfect E. coli K 12-JM 101 cells. Forty-two white plaques, picked at random, were used for preparation of template DNA and sequenced, yielding a continuous sequence of 2379 nucleotides (FIG. 2).

In order to keep an open reading frame, an extra nucleotide had to be introduced around position 595–600. This area was sequenced several times on both strands and unambiguously gave the sequence TGTAAAATGGT (position 592–601). Protein sequencing in this region gave the sequence CMCys-Lys-Asn-Gly, which indicates that one nucleotide (A) had been artifactually deleted at position 595–599, presumably during the preparation of the cDNA library.

cDNA FOR HUMAN PROTEIN S

A human fetal liver cDNA library in lambda gt 11 was prepared by a modification of the procedure of Gubler and Hoffman (1983, Gene 25:263), similar to that described by Lapeyre and Amalric (1985, Gene, 37:215). The library contained over $6 \times 10^7$ recombinants with inserts averaging 1800 nucleotides in length. Plaques from the amplified library were screened using standard techniques. Nick translated DNA fragments from a bovine Protein S cDNA clone, pBLS-2400 (FIG. 1) and a human Protein C cDNA clone obtained from Robert Wydro of Integrated Genetics, Inc. (Wydro et al., described in detail in (Wydro et al. application Ser. No. 51,366 assigned to the same assignee as this application) were used as probes.

Figure 1:
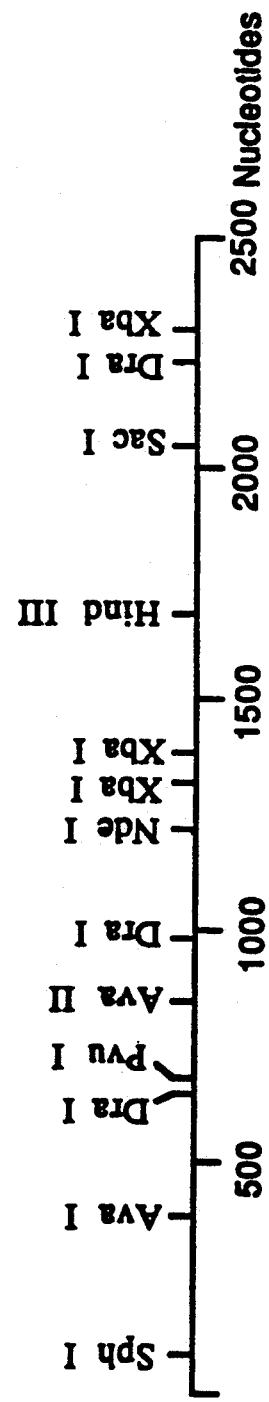
FIG. 1 is a restriction map for the full length bovine protein S clone, pBLS-2400.
Figure 3:
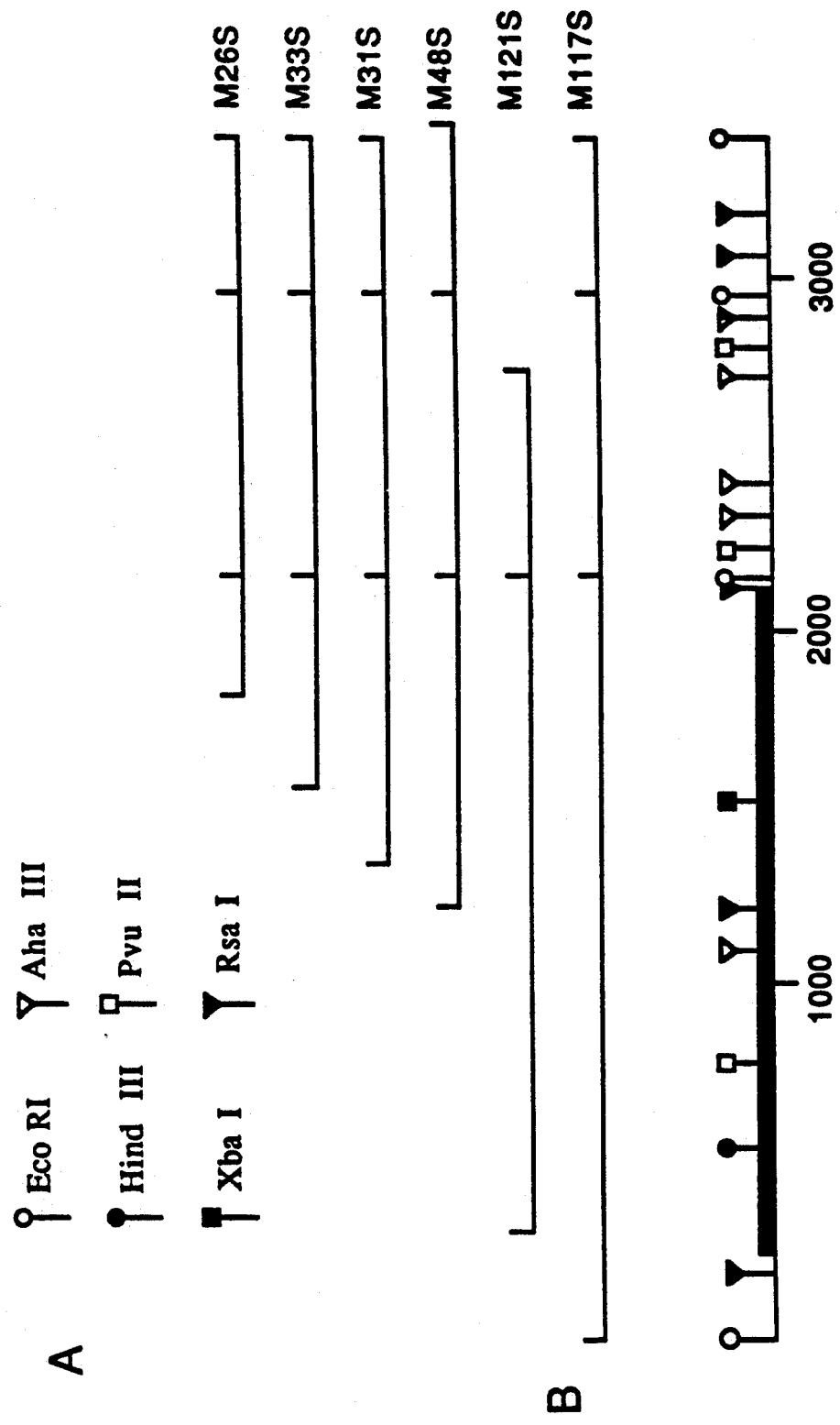
FIG. 3 is a restriction map for human Protein S cDNA clones; (A) diagram representing the isolated λ gt 11 cDNA clones coding for human Protein S; (B) partial restriction map for Protein S cDNA; the thick line represents those sequences that code for Protein S.

Approximately $1 \times 10^6$ plaques of the human λgt11 library were screened using the SphI-SacI fragment (coding for amino acids −29 to 620) from pBLS-2400 (FIG. 1) Four positive clones, designated M26, M31, M33 and M48 (FIG. 3) were plaque purified and characterized. These clones were confirmed as coding for human protein S by comparison to the bovine Protein S cDNA sequence, to which they showed significant homology. The EcoRI-XbaI fragment (coding for amino acids 311 to 403) from the the clone M48S was then used to screen 18 million plaques from the λgt11 library. Thirty-nine positives were identified. To distinguish those human clones that contained inserts coding for the 5' region of the mRNA, successive hydridizations were performed with DNA fragments of pBLS-2400 containing 5' end sequences, e.g., the SphI-AvaII fragment. Four clones hybridized with the 5' coding sequences from the bovine cDNA. Of these, three were subsequently shown to be identical. These clones, typified by M117S (FIG. 3) lacked only the coding region for the first 26 amino acids of the leader peptide, as evidenced by a comparison to the bovine sequence.

HUMAN PROTEIN S cDNA SEQUENCE

The total cloned Protein S cDNA contained 3,344 bp and coded for amino acids −15 of the leader sequence to the termination codon after Ser (amino acid 635). The nucleotide sequence of the human Protein S cDNA and the derived amino acid sequence are given in FIG. 4. The cDNA contained a 1,148 bp 3' untranslated region, which was 826 bp longer than its bovine counterpart. The homology between the bovine and the human Protein S cDNA clones extends through all of the 3' untranslated region of the bovine cDNA up to, but not including the poly(A) tail. Northern blot data suggests the existence of only one major molecular weight species of human Protein S mRNA. Although the possibility of extended 5' untranslated sequences cannot be excluded, the 3' untranslated region could account for all of the size difference between the human and bovine Protein S mRNA's.

The entire cloned human Protein S cDNA sequence when aligned with the bovine cDNA sequence contains a 244 bp 5' sequence which differs to a large degree from the bovine sequence. The overall homology between the nucleic acid sequences of the mature human and bovine Protein S is 87.5% and homology between the protein sequences is 81.6%.

CONSTRUCTION OF pUC9XBHS

In order to insert human Protein S cDNA into expression vectors, unique restriction enzyme sites, as well as a complete leader sequence, were engineered onto the 5' and 3' ends of the human Protein S clone.

The restriction enzyme site Xho I is very rare in nature and is not present in the human Protein S coding sequence. This restriction enzyme had been used previously to insert genes into vectors containing the transforming BPV virus (Wei et al., application Ser. No. 782,686, filed Oct. 1, 1985, assigned to the same assignee as this application, and hereby incorporated by reference). Since the human Protein S cDNA did not encode the full leader peptide, and this peptide may be necessary for post-translational modifications, the leader sequence of the bovine Protein S was spliced onto the human Protein S cDNA, preserving as much of the human cDNA as possible. The bovine leader sequence also may have closer homology than the human sequence to the corresponding rodent sequences, providing potential expression and processing advantages where the mammalian expression system used is of rodent origin.

Due to the nature of distribution of the restriction enzyme sites in the bovine and human Protein S cDNA sequences, a multiple step construction was necessary to engineer the bovine leader sequence onto the human cDNA with the necessary Xho I sites at the 5' and 3' ends of the final construction. The procedure used is illustrated in FIGS. 5 through 8, and was carried out as follows.

I. Construction of the Bovine Leader Sequence (Piece 1)

Referring to FIG. 5, the bovine Protein S cDNA clone pBLS2400 was restricted at a unique site with the enzyme AvrII. To prevent self-ligation of the linear DNA during the next set of experiments, the terminal phosphates were removed with bacterial alkaline phosphatase (BAP). Two synthetic oligonucleotides, BD382 (5'-CTAGGACCCTCATC-3') and BD 383 (5'-TCGAGATGAGGGTC-3'), containing terminal phosphate groups, were annealed and ligated in the presence of the linear pBLS2400. The desired construction contains a dimer of the annealed oligonucleotides inserted into the AvrII site of pBLS2400, generating an XhoI site. This construction, named pBLS2400X, was digested with XhoI and TaqI, and an 87 bp 5'-end piece isolated from low-melting point (LMP) agarose gel using a modification of the procedure described by Langridge et al. (1980, Anal. Bioch: 103:264–271), as described below. This 87 bp fragment contains the initiator methionine and encodes the leader signal sequence of bovine Protein S. It is designated "Piece 1".

DNA EXTRACTION

QN+-aqueous and QN+-butanol were prepared as follows. 2 g of hexadecyltrimethylammonium bromide (QNBr) were dissolved in 100 ml n-butanol, 100 ml $H_2O$ and 50 µl antifoam A(Sigma), vigorously shaken, and allowed to separate overnight. The upper layer, defined as QN+-butanol, and the lower layer, defined as QN+-aqueous, were bottled separately.

The procedure includes the following steps.

A band is cut out from a low melting point (LMP) agarose gel; melted at 70° C. for about 3 min; an equal volume of QN+-aqueous and QN+ butanol added, the solution vortexed and centrifuged in a microfuge for 1-2 min; the butanol (upper) phase removed to a fresh tube; the QN+-aqueous-agarose phase reheated to 70° C. for 2-3 min, and re-extracted once with QN+-butanol; ¼ volume of 0.4M NaCl added to the combined butanols, the mixture vortexed and spun briefly in a microfuge; the aqueous (lower) layer transfered to a fresh tube; extraction with chloroform; and the DNA precipitated with ethanol.

II. Construction of Piece 2

To join the human Protein S cDNA with the bovine Protein S Leader (Piece 1), a TaqI site was created in the human cDNA at an appropriate site. To accomplish this mutation, the human Protein S cDNA clone 117S-1 (the 2,200 bp EcoRI fragment from M117S subcloned into pUC18) was digested with EcoRI and HindIII. A 580 bp fragment was isolated from a LMP agarose gel and further digested with RsaI. (The 1600 bp fragment was also isolated from an LMP agarose gel and used in the construction of Piece 3, as described below.) The 380 bp fragment generated was isolated from an LMP agarose gel and ligated into the vector mp18 which was previously digested with SmaI and HindIII, to give mp18-2ori. The single-stranded form of mp18-2ori was isolated and the appropriate base pair changed by site directed mutagenesis using a synthetic oligonucleotide BW363, as described below. The mutation was identified by hybridization analysis and a clone (termed mp18-2mut) isolated in bulk quanitities.

In order to construct the additional TaqI site in the human Protein S cDNA, 3.4 µg of mp18-2ori and 1.4 µg of kinased oligonucleotide BW 363 (5'-TGAAGCCTGTTGCTTCGACAAAACTCTTCC-3') were annealed in 30 µl of 0.2M Tris-HCl, pH7.5; 0.1M $MgCl_2$; 0.5M NaCl and 10 mM DTT by heating to 65° C. for 10 minutes and then slowly cooled to room temperature over a two hour period.

The second strand of the phage DNA was synthesized by adding 50 µl of buffer (20 mM Tris,pH7.5; 10 mM $MgCl_2$; 10 mM DTT; 2.5 mM each of dATP, dCTP, dGTP and dTTP), along with 5 µl of 20 mM ATP, 1 µl T4 Ligase (400,000 units), 3.5 µl *E. coli* DNA polymerase, Klenow fragment (14 units), and 10.5 µl of distilled water. The mixture was incubated at room temperature for 15 minutes, then overnight at 15° C.

In order to reduce the background of vector which has not been made double stranded by the above priming and extension reaction, about 20 µl of the above extension reaction was mixed with 58 µl of water, and 20 µl of buffer containing: 1.5M NaCl; 0.25M Na Acetate, pH 4.6; 15% glycerol, 1 µl of *E.coli* tRNA(2µ/µl), and 1 µl of Sl nuclease (2.65 units). After incubation at 37° C. for 30 minutes the reaction was terminated by the addition of 1 µl of 500 mM EDTA and 50 µl of TE (Tris 10 mM, pH 8; EDTA 1 mM). The mixture was phenol-cholorform extracted and the DNA precipitated from the aqueous phase with ethanol. The precipitated DNA was dissolved in 10 µl of TE.

This Sl treated extension was transformed into competent JM101 *E. coli* cells. Mutants were identified using filter lifts on the plates containing the plaques from the Sl treated extension reaction. The synthetic oligonucleotide BW363 was kinased to a high specific activity with $^{32}P$-ATP and used as a hybridization probe in a solution containing: 0.74M NaCl; 0.05M $NaH_2PO_4$, pH 7.4; 5 mM EDTA; 5×Denhardt's solution; 0.1% SDS; and 100 µg/ml Torula RNA. Hybridization was at 40° C. overnight. The filters were washed with several changes of 1×SSC/0.1% SDS at 57° C. The resulting filters were autoradiographed, the autoradiograph aligned to the culture plate, and a strongly hybridizing plaque picked and grown overnight in 5 ml of medium. A plasmid mini-prep was performed to isolate the double stranded Rf form of the phage and the mutant confirmed by DNA sequence analysis. The phage DNA was digested with EcoRI and HindIII and a 400 bp fragment containing the new mutation isolated from a LMP agarose gel. This DNA fragment was cloned into pUC18 previously digested with EcoRI and HindIII. This new plasmid was termed pUC18mut2S.

DNA consisting of a 430 bp TaoI-PvuII fragment containing an internal unrestricted TaqI site was generated from a 490 bp EcoRI-PvuII DNA fragment of pUC18mut2S as follows: Separate aliquots containing 1 µg of the 490 bp DNA fragment in 10 µl total volume were digested at 55° C. with 0.8 units of TaqI for 15, 20, 25, 30 and 35 minutes respectively; four separate aliquots each containing 4 µg of the 490 bp DNA fragment in 27 µl were restricted at 65° C. for 15 minutes with 0.8, 1.6, 2.4, and 3.2 units respectively of TaqI; four separate aliquots each containing 4 µg of the 490 bp DNA fragment in a total of 27 µl were restricted at 65° C. for 15 minutes with 3.2 units of TaqI; and two separate aliquots each containing 4 µg of the 490 bp DNA fragment in a total of 27 µl were restricted at 65° C. for 15 minutes with 3.9 units of TaqI. After enzymatic treatment, the DNA of each aliquot was electrophoresed in a 0.9% LMP agarose gel, bands containing the 430 bp fragment were excised from the gel and pooled. To insure purity of the fragment and facilitate joining to Piece 3 (below), the 430 bp DNA fragment was digested with HindIII and the resulting 330 bp fragment isolated. This fragment was designated "Piece 2".

III. Construction of Piece 3

To complete the contruction, the 3' end of the clone needed to be altered to establish an XhoI cloning site. To accomplish this, two oligonucleotides were made which, when annealed, constitute a linker that can ligate to a 3' EcoRI site, replacing the missing nucleotides and the termination codon, and add an XhoI site. This was performed using the 1600 bP HindIII-EcoRI fragment isolated from 117S-1 as described above, and the synthetic oligonucleotides EC347 (5'-AATTCT-TAAGCTCGAGC-3') and EC348 (5'-GCTCGAGCTTAAG-3').

The oligonucleotides were annealed and ligated to the 1600 bp HindIII-EcoRI fragment using techniques analogous to those described above. After ligation, the DNA was digested with HindIII and XhoI and a 1600 bp DNA fragment isolated from a LMP agarose gel. This DNA fragment was cloned into pUC9X (pUC9 digested with SmaI and an XhoI linker added) which had previously been digested with HindIII and XhoI. Chimeric plasmids were identified by restriction analysis, and one clone isolated and grown in bulk. This plasmid was then digested with HindIII and XhoI and the 1600 bp insert isolated from LMP agarose gel. This 1600 bp HindIII-XhoI DNA fragment is designated "Piece 3".

IV Contruction of pUC9XBHS

Piece 1 and Piece 2 were ligated together, digested with XhoI and HindIII, electrophoresed on a 1.4% LMP agarose gel, and the 430 bp DNA fragment excised from the gel. This fragment was then ligated into pUC9X previously digested with XhoI and HindIII. The chimeric plasmid was identified by restriction analysis and a clone (termed pUC9X-Hl-2S) isolated.

pUC9X-Hl-2S was restricted with HindIII and XhoI and the 430 bp DNA fragment isolated from a LMP agarose gel. This fragment was ligated to Piece 3 and the resulting DNA digested with XhoI and electrophoresed in a 0.8% LMP agarose gel. The 2,000 bp DNA fragment was excised from the gel, and cloned into pUC9X which had been digested with XhoI and treated with BAP. The desired clone was identified by restriction analysis and one clone (termed pUC9XBHS) isolated in bulk quantities.

Insertion of Protein S Into Expression Vectors

The modified cDNA in pUC9XBHS can be inserted into any suitable mammalian expression vector, most preferably rodent epithelioid cells. Preferred expression vectors are the BPV vectors described in Wei et al. supra, and Hsiung et al. 1984, J. Molec. and App. Genet. 2:497. The vectors (FIG. 9) include a mouse metallothionein promoter (MT) from which inserted genes can be transcribed, and bovine papilloma virus DNA (BPV) to effect transfection of mammalian cells. CLH3axBPV also includes late promoter poly-adenylation sequences derived from SV40, which can affect expression from a gene inserted into the vector. The illustrated expression plasmids also include a portion of the E. coli plasmid pML, which permits shuttling between procaryotic and eucaryotic systems. No selection is required for the maintenance of these plasmids in host cells, and they are maintained in high (approximately 100 copies/cell) copy number.

The XhoI-linkered Protein S sequence in pUC9XBHS was isolated by digestion with XhoI and excision of the insert band from an agarose gel. This fragment was then cloned into the XhoI site of each of the two BPV vectors. These vectors were then transformed into E. coli strain MC1061 and grown in bulk culture. The DNA was purified by CsCl banding before transfection into mammalian cells. The 5' to 3' orientation of the Protein S insert within the expression vectors was checked by numerous sets of restriction enzyme digestions. The final vector constructs are shown in FIG. 9. As a matter of convenience, the names of the expression vectors have been shortened to CSM and CSS for CL28XhoBPVProS and CLH3axBPVProS, respectively.

MAMMALIAN EPITHELIOID CELL TRANSFECTION

On 5 separate days, two sets of transfections into mouse C127 cells were carried out as follows:

Mouse C127 cells (commercially available) were maintained in Dulbecco's modified Eagle's medium (DME) supplemented with 10% fetal calf serum and 10 mM glutamine as described in Hsiung et al., id. DNA transfections were carried out by the method described in Wilger et al. 1977, Cell 11:233, as modified by Hsiung et al., id. Ten to twenty micrograms of calcium phosphate precipitated DNA was incubated for 6–8 hours at 37° C. with $1 \times 10^6$ cells in fresh culture medium. The medium was removed and the cells treated with 20% glycerol in 10 mM phosphate-buffered saline (PBS), pH 7.0, for 1–2 minutes at room temperature, washed twice with PBS and fresh DME added. The cells (designated CL28X) were then incubated at 37° C. and the medium replaced after 24 hours and every 3–4 days thereafter.

PROTEIN S EXPRESSION

Ten days after transfection the culture medium was tested in an ELISA assay for human Protein S. In this assay a 1/10,000 dilution of rabbit anti-human Protein S antiserum was used to coat microtiter wells (Immulon), 200 μl per well, overnight at room temperature. After washing the wells extensively with buffer containing PBS/Tween, the wells were "blocked" for 2 hours with 200 μl of 2% bovine serum albumin (BSA) in PBS (phosphate buffered saline). After washing, the wells were challenged with 200 μl of culture medium from the CSM transfected cells. The culture medium was incubated in the wells for four hours at room temperature. After washing, 200 μl of goat anti-human Protein S was added to the wells and incubated overnight at room temperature. The wells were again washed, and 200 μl of rabbit anti-goat IgG antibodies conjugated with horseradish peroxidase (HRP) was added. Incubation was for 2 hours at room temperature before washing and adding 200 μl of the HRP substrate, orthophenylene diamine (OPD). The HRP reaction was terminated by the addition of 50 μl of 3M $H_2SO_4$. The microtiter wells were then read with a microtiter well reader set at 492 nm. The results, given in the table below, demonstrate that Protein S is produced by the transfected cells. (The transfected cells are isolates CL28XA1A[2], CL28XB1A[3], CL28XB1B[4], CL28XB2C[5], and CL28XB2A[6] in the table.).

| Sample | Average Absorption(1) at 492 nm | Approximate ng/ml hProtein S |
| --- | --- | --- |
| C127 cells untransformed | 0.371 | 0 |

-continued

| Sample | Average Absorption(1) at 492 nm | Approximate ng/ml hProtein S |
|---|---|---|
| 12.5 ng hProtein S | 1.427 | 12.5 |
| 1.25 ng hProtein S | 0.468 | 1.25 |
| CL28XA1A(2) | 0.396 | 0 |
| CL28XB1A(3) | 0.555 | 2.1 |
| CL28XB1B(4) | 0.649 | 3.2 |
| CL28XB2C(5) | 0.719 | 4.0 |
| CL28XB2A(6) | 0.677 | 3.5 |

PURIFICATION AND USE

Human Protein S produced in transfected cells as described above is purified from the cells and/or the culture medium according to conventional techniques, e.g., as described in Comp et al. (1984, J. Clin. Invest. 74, 2082). The human Protein S so produced, because it is derived from mammalian cells, is free of C4-binding proteins as well as bacterial and viral pathogens.

THERAPEUTIC USE

Human Protein S can be lyophilized and reconstituted in saline prior to use. Protein S in saline can be administered on a regular basis (e.g., weekly) to human patients congenitally deficient in Protein S, to inhibit the recurrent thrombosis seen in these patients. Administration is by the modes of administration used for other anti-thrombolytic agents, e.g., tissue plasminogen activator. Most preferably, administration is by bolus injection or by intravenous infusion. The following examples are illustrative.

EXAMPLE 1

For long-term maintainance of a human patient deficient in Protein S, 150 mg of lyophilized Protein S are dissolved in saline and placed in the chamber of a syringe, which is used to inject a bolus of Protein S into the patient intravenously; treatment is carried out once per week.

EXAMPLE 2

For infusion treatment for the rapid lysis of coronary thrombi, about 100 mg/hr of lyophilized t-PA, about 1.0 mg/hr of lyophilized Protein C, and about 2.0 mg/hr of lyophilized Protein S are dissolved in saline and infused at the same time, together or via separate infusion lines, intravenously over a period of about 3 hours.

EXAMPLE 3

For infusion treatment for the slow lysis of deep vein thrombi, about 10 mg/hr of lyophilized t-PA, about 1.0 mg/hr of lyophilized Protein C, and about 2.0 mg/hr of lyophilized Protein S dissolved in saline are infused, at the same time, together or via separate infusion lines, intravenously over a period of about 12-24 hours.

DIAGNOSTIC USE

Antibodies, either polyclonal or monoclonal, can be raised to Protein S and used in conventional immunoassay methods to quantify Protein S in biological fluids, e.g., serum or urine, of patients suspected of having a protein S deficiency.

DEPOSITS

E. coli cells containing the plasmid CSM have been deposited with the American Type Culture Collection, Rockville, Md., and assigned ATCC Accession Number 67163.

Applicants' assignee, Integrated Genetics, Inc., acknowledges its responsibility to replace this culture should it die before the end of the term of a patent issued hereon, 5 years after the last request for a culture, or 30 years from the date of deposit, whichever is the longer, and its responsibility to notify the depository of the issuance of such a patent, at which time all restrictions on the availability to the public of the material so deposited will be irrevocably removed. Until that time the deposit will be made available to the Commissioner of Patents under the terms of 37CFR Section 1-14 and 35USC Section 112.

Other embodiments are within the following claims.

We claim:

1. A cDNA sequence encoding mature human Protein S.

2. A vector comprising a DNA sequence encoding mature human Protein S.

3. The vector of claim 2 wherein said DNA sequence encoding mature human Protein S is under the transcriptional control of a promoter of an eukaryotic metallothionein gene.

4. A mammalian cell transfected with the vector of claim 2.

5. The mammalian cell of claim 4 wherein said cell is an epithelial cell.

6. The mammalian cell of claim 4 wherein said cell is a rodent cell.

7. The mammalian cell of claim 6 wherein said cell is a mouse cell.

8. The vector of claim 2, said vector further comprising at least the 69% transforming regino of the bovine papilloma virus genome.

9. The vector of claim 8 wherein said vector contains all of said bovine papilloma virus genome.

10. A method for producing mature human Protein S, comprising the steps of:
   a) transfecting mammalian cells with the vector of claim 1
   b) culturing said mammalian cells under conditions in which said mammalian cells produce protein, and
   c) isolating said Protein S from said mammalian cells and the culture medium.

11. The method of claim 10 wherein said DNA encoding mature human Protein S is cDNA.

* * * * *

UNITED STATES PATENT AND TRADEMARK OFFICE
CERTIFICATE OF CORRECTION

PATENT NO. : 5,258,288

DATED : November 2, 1993

INVENTOR(S) : Robert Wydro, et al

It is certified that error appears in the above-identified patent and that said Letters Patent is hereby corrected as shown below:

Column 10, line 52, cancel, "claim 1" and insert therefor --claim 2--.

Signed and Sealed this

Seventeenth Day of May, 1994

Attest:

BRUCE LEHMAN

Attesting Officer    Commissioner of Patents and Trademarks